US006376678B1

(12) United States Patent
Sugi et al.

(10) Patent No.: US 6,376,678 B1
(45) Date of Patent: Apr. 23, 2002

(54) PRODUCTION METHOD OF HYDRAZINE DERIVATIVE

(75) Inventors: Kiyoshi Sugi; Kozo Matsui; Tetsuya Shintaku; Nobushige Itaya, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/521,058

(22) Filed: Mar. 8, 2000

(51) Int. Cl.$^7$ .................. C07D 211/70; C07C 241/00
(52) U.S. Cl. ........................ 546/329; 564/313
(58) Field of Search ................ 546/332, 329; 564/313

(56) References Cited

FOREIGN PATENT DOCUMENTS

| GB | 924600 | * | 4/1963 |
| WO | 97/40029 | | 10/1997 |

OTHER PUBLICATIONS

Lawton, et. al., "Synthesis of 1,2–Diazetidinones (Aza–B–lactams) by Photochemical Ring Contraction", J. Chem. Soc. Perkin Trans. 1, pp. 877–883, 1987.*

* cited by examiner

Primary Examiner—Alan L. Rotman
Assistant Examiner—Binta Robinson
(74) Attorney, Agent, or Firm—Leydig, Voit & Mayer, Ltd.

(57) ABSTRACT

A production method of hydrazine derivative having a group of the formula (II)

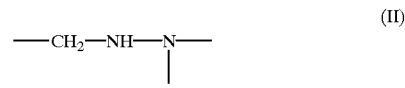

which comprises subjecting a hydrazone derivative having a group of the formula (I)

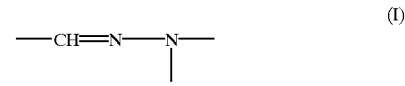

to catalytic reduction and deactivating the reduction catalyst contained in the reaction mixture thereof. According to the production method of the present invention, which is industrially superior, hydrazine derivative (II) stable even in a solution state can be produced

15 Claims, No Drawings

PRODUCTION METHOD OF HYDRAZINE DERIVATIVE

TECHNICAL FIELD OF THE INVENTION

The present invention relates to a production method of a hydrazine derivative having a group of the formula (II)

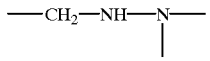

(II)

which is stable even in a solution state.

BACKGROUND OF THE INVENTION

A hydrazine derivative having a group of the formula (II)

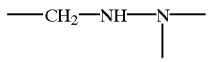

(II)

(hereinafter is to be also referred to as hydrazine derivative (II)) can be generally obtained by subjecting a hydrazone derivative having a group of the formula (I)

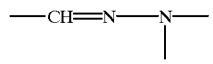

(I)

(hereinafter to be also referred to as hydrazone derivative (I)) to catalytic reduction. When the hydrazine derivative (II) obtained by a known method is preserved in a suitable organic solvent, such as isopropyl alcohol, the hydrazine derivative (II) converts to the hydrazone -drivative (I) and becomes an impurity in the next step. Thus a production method of hydrazine derivative (II), which is stable even in a solution state, has been desired.

In addition, tert-butyl3-[4-(pyridin-2-yl)benzyl]carbazate of the formula

(IIb)

wherein tBu is tert-butyl (hereinafter to be also referred to as a hydrazine derivative (IIb), which is among the hydrazine derivatives (II), is useful as a synthetic intermediate for compound (A) of the formula

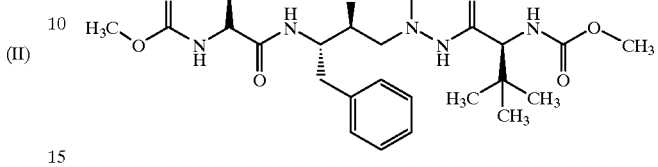

(A)

which is an anti-HIV drug. For example, N-(tert-butoxycarbonyl)-N'-[4-(pyridin-2-yl )phenylmethylidene] hydrazine of the formula (Ib)

wherein tBu is tert-butyl [hereinafter to be also referred to as hydrazone derivative (Ib)], which is among the hydrazone derivatives (I), can be treated by the method described in WO97/40029 to give the medicament of compound (A) via hydrazine derivative (IIb).

SUMMARY OF THE INVENTION

It is therefore an object of the present invention to provide a production method of hydrazine derivative (II) which is stable even in a solution state.

Such object can be achieved by the following invention which affords a method comprising subjecting a hydrazone derivative (I) to catalytic reduction and deactivating the reduction catalyst contained in the reaction mixture thereof. According to the method of the present invention, a hydrazine derivative (II), which is free of hydrazone derivative (I) and which is stable even in a solution state, can be obtained by preserving the derivative in an organic solvents Accordingly the present invention provides (1) a production method of hydrazine derivative having a group of the formula (II)

(II)

—CH₂—NH—N— which comprises subjecting a hydrazone derivative having a group of the formula (I)

(I)

—CH═N—N— to catalytic reduction and deactivating the reduction catalyst contained in the reaction mixture thereof; (2) the production method of (1) above, wherein the hydrazone derivative (I) is a hydrazone derivative (Ia) of the formula

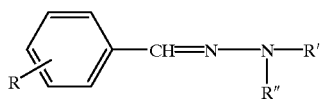

(Ia)

wherein R is hydrogen atom, halogen atom, alkyl having 1 to 4 carbon atoms, alkoxy having 1 to 4 carbon atoms, optionally substituted aryl or optionally substituted aromatic heterocyclic group, R' is hydrogen atom, acyl, alkoxycarbonyl, alkyl -or optionally substituted phenyl and R" is acyl, alkoxycarbonyl, alkyl or optionally substituted phenyl, and the hydrazine derivative (II) is a hydrazine derivative (IIa) of the formula

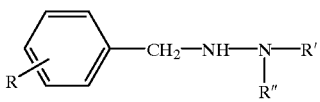

(IIa)

wherein R, R' and R" are as defined above; (3) the production method of (1) above, wherein the step for deactivating the reduction catalyst comprises the use of a catalytic poison and/or an adsorbent, (4) the production method of (3) above, wherein the catalytic poison is a sulfur compound; (5) the production method of (4) above, wherein the sulfur compound is sodium hydrosulfite, (6) the production method of (3) above, wherein the adsorbent is an active charcoal, (7) the production method of (1) above; which further comprises, after deactivation of the reduction catalyst, recrystallizing in a solvent containing a saturated hydrocarbon solvent and (8) the production method of any of (1)–(7) above, wherein the hydrazine derivative (II) is tert-butyl3-[4-(pyridin-2-yl)benzyl]carbazate.

DETAILED DESCRIPTION OF THE INVENTION

The terms and substituents used in the present specification are defined in the following.

A typical catalytic poison is a substance that strikingly reduces or eliminates the activity of a catalyst used in a catalytic reaction. As used in this specification, the catalytic poison eliminates the catalytic activity.

As used in this specification, by halogen atom is meant, unless particularly specified, a fluorine atom, chlorine atom, bromine atom or iodine atom.

As used in this specification, by alkyl is meant, unless particularly specified, a linear or branched chain alkoxy having 1 to 4 carbon atoms, such as methyl, ethyl, propyl, isopropyl, butyl, isobutyl, sec-butyl and tert-butyl.

As used in this specification, by alkoxy is meant, unless particularly specified, linear or branched chain alkyl having 1 to 4 carbon atoms, such as methoxy, ethoxy, propoxy, isopropoxy, butoxy, isobutoxy, sec-butoxy and tert-butoxy.

As used in this specification, by alkoxycarbonyl is meant, unless particularly specified, alkoxycarbonyl having 2 to 5 carbon atoms wherein the alkoxy moiety is linear or branched chain alkoxy. Examples thereof include methoxycarbonyl, ethoxycarbonyl, propoxycarbonyl, isopropoxycarbonyl,. butoxycarbonyl, isobutoxycarbonyl, sec-butoxycarbonyl and tert-butoxycarbonyl.

The halogen atom at R is a fluorine atom, chlorine atom, bromine atom or iodine atom, preferably a fluorine atom, chlorine atom or bromine atom.

The alkyl having 1 to 4 carbon atoms at R is linear or branched chain alkyl having 1 to 4 carbon atoms, such as methyl, ethyl, propyl, isopropyl, butyl, isobutyl, sec-butyl and tert-butyl, preferably tert-butyl.

The alkoxy having 1 to 4 carbon atoms at R is linear or branched chain alkoxy having 1 to 4 carbon atoms, such as methoxy, ethoxy, propoxy, isopropoxy, butoxy, isobutoxy, sec-butoxy and tert-butoxy, preferably methoxy and ethoxy.

The optionally substituted aryl at R is aryl optionally having the following 1 to 3, preferably 1 or 2, substituents, without particular limitation on the substitution site. As aryl, exemplified are phenyl and naphthyl. The substituent may be any as long as it is not reduced by the catalytic reduction used in the present inventions. Examples thereof include alkyl, alkoxy, halogen atom, carboxy, alkoxycarbonyl and cyano. The optionally substituted aryl is exemplified by phenyl, 2-, 3- or 4-tolyl, 2-, 3- or 4-methoxyphenyl, 2-, 3- or 4-fluorophenyl, 2-, 3- or 4-chlorophenyl, 2-, 3- or 4-carboxyphenyl and 2-, 3- or 4-cyanophenyl, preferably phenyl The optionally substituted aromatic heterocyclic group at R is an aromatic heterocyclic group optionally having the following 1 to 3, preferably 1 or 2, substituents. The aromatic heterocyclic group is that having at least one hetero atom selected from the group of N, O, and S, such as furyl, oxazolyl, imidazolyl, pyridyl and pyrimidinyl. The substituent may be any as long as it is not reduced by the catalytic reduction used in the present invention, without particular limitation on the substitution site. Examples thereof include alkyl, alkoxy, halogen atom, carboxy, alkoxycarbonyl and cyano. The optionally substituted aromatic heterocyclic group may be 2-, 3-or 4-pyridyl, preferably 2-pyridyl.

The acyl at R' and R" may be, for example, formyl, acetyl, propionyl, butyryl or benzoyl, preferably acetyl or benzoyl.

The alkoxycarbonyl at R' and " is that having 2 to 5 carbon atoms, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, preferably tert-butoxycarbonyl.

The alkyl at R' and R" is linear or branched chain alkyl having 1 to 8, preferably 1 to 4, carbon atoms, such as methyl, ethyl, propyl, isopropyl, butyl, isobutyl sec-butyl, tert-butyl, pentyl, isopentyl, neopentyl, tert-pentyl, hexyl, isohexyl, heptyl and octyl, preferably methyl, ethyl and propyl.

The optionally substituted phenyl at R' and R" is phenyl optionally having the following 1 to 3, preferably 1 or 2, substituents, without particular limitation on the substitution site. The substituent may be any as long as it is not reduced by the catalytic reduction used in the present invention. Examples thereof include alkyl, alkoxy, halogen atom, carboxy and alkoxycarbonyl. The optionally substituted phenyl is exemplified by phenyl, 2-, 3- or 4-tolyl, 2-, 3- or 4-alkoxyphenyl, 2-, 3- or 4-halophenyl and 2-, 3- or 4-carboxyphenyl, preferably phenyl.

The present invention is explained in detail in the following.

In the inventive method, catalytic reduction of hydrazone derivative (I) can be carried out according to a known method. For example, hydrazone derivative (I) is subjected to catalytic reduction in a suitable reaction solvent in the presence of a catalyst under a hydrogen atmosphere. After the catalytic reduction, the catalyst is filtered off from the reaction mixture, and the solvent as evaporated by concentration and/or the filtrate is crystallized to give hydrazine derivative (II). After the catalytic reduction, the reduction catalyst in the reaction mixture is deactivated to afford a hydrazine derivative (II) that is stable even in a solution state.

The hydrazone derivative (I) of the present invention may be, for example, hydrazone derivative (Ia) of the formula

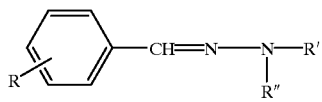

(Ia)

wherein R is hydrogen atom, halogen atom, alkyl having 1 to 4 carbon atoms, alkoxy having 1 to 4 carbon atoms, optionally substituted aryl or optionally substituted aromatic heterocyclic group, R' is hydrogen atom, acyl, alkoxycarbonyl, alkyl or optionally substituted phenyl and R" is acyl, alkoxycarbonyl, alkyl or optionally substituted phenyl. The hydrazone derivative (Ia) may be, for example, N-(tert-butoxycarbonyl)-N'-[4-(pyridin-2-yl)phenylmethylidene]hydrazine.

The hydrazine derivative (II) in the present invention may be, for example, hydrazine derivative (IIa) of the formula

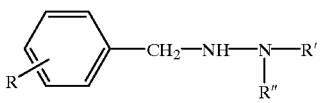

(IIa)

wherein R, R' and R" are as defined above. The hydrazine derivative (IIa) may be, for example, tert-butyl3-f4-(pyridin-2-yl)benzyl]carbazate.

The catalyst to be used for catalytic reduction may be any as long as it is generally used in this field. Examples thereof include palladium catalysts such as palladium-carbon, palladium black and the like platinum catalysts such as platinum carbon, platinum black and the like, rhodium catalyst, ruthenium catalyst and nickel catalysts such as Raney nickel and the like, preferably palladium-carbon.

The catalyst is used in an amount of 1 wt %–10 wt %, preferably 3 wt %–6 wt %, of part by weight of hydrazone derivative (I).

The solvent to be used for catalytic reduction may be any as long as it is generally used in this field. Examples thereof include alcohol solvents such as methanol, ethanol, isopropyl alcohol, butanol, tert-butyl alcohol and the like, ether solvents such as tetrahydrofuran, diethyl ether, 1,2-dimethoxyethane and the like, aromatic hydrocarbon solvents such as toluene, benzene and the like, with preference given to alcohol solvents, particularly preferably isopropyl alcohol.

The solvent is used in an amount of 2 parts by weight–10 parts by weight, preferably 3 parts by weight–6 parts by weight, per part by weight of hydrazone derivative (I).

The catalytic reduction is carried out in a temperature range of 10–70° C., preferably 40–50° C.

The catalytic reduction is carried out from atmospheric pressure to 5 atm., preferably from atmospheric pressure to 2 atm.

The completion of catalytic reduction can be confirmed by disappearance of the peak of the starting compound of hydrazone derivative (I) by, for example, HPLC.

For a hydrazine derivative (II) stable even in a solution state to be obtained, the reduction catalyst contained in the reaction mixture is deactivated after confirmation of the completion of the catalytic reduction. This step preferably includes the use of a catalytic poison and/or an adsorbent. From the aspect of deactivation, the concurrent use of a catalytic poison and an adsorbent is more preferable.

The catalytic poison to be used in the present invention may be any as long as it is generally known. Examples thereof include a simple substance belonging to the Va group (P, As, Sb, Bi) or VIa group (S, se, Te) and derivatives thereof. For easy handling, a sulfur compound is preferable.

The sulfur compound to be used in the present invention may be a simple substance of sulfur, carbon disulfide, a derivative having —SH group, a derivative potentially having —SH group or a derivative having S—S bond, preferably a derivative potentially having —SH group.

The derivative having —SH group has one or more —SH groups. Examples thereof include hydrogen sulfide, salt of thiol (e.g., NaSH, NH$_4$SH, KSH and the like), alkanethiol (e.g., methanethiol, ethanethiol, propanethiol and the like), arenethiol (e.g., benzenethiol and the like) and derivatives having two or more —SH groups (e.g., methanedithiol, ethanedithiol and the like).

The derivative potentially having —SH group is a derivative that originally does not have —SH group but comes to have one by neutralization or substitution of the counter ion with hydrogen atom. Examples thereof include a derivative having —SNa group, since —SNa group becomes —SHf group by neutralization. Specific examples thereof include sodium sulfide, ammonium sulfide and sodium hydrosulfite, preferably sodium hydrosulfite.

The derivative having S—S bond has one or more S—S bonds. Examples thereof include organic disulfide derivative (e.g., dimethyl disulfide, diphenyl disulfide and the like), organic polysulfide derivative having 3 or more sequential S—S bonds and inorganic polysulfide derivative (e.g., ammonium polysulfide and the like).

The amount of the catalytic poison varies depending on the kind of catalytic poison, and the kind and amount of catalyst used, and the catalytic poison can be added until the catalyst used becomes deactivated. For example, when palladium-carbon is used as a reduction catalyst in an amount of 5 wt % of part by weight of hydrazone derivative (I) and sodium hydrosulfite is used as a catalytic poison, the catalytic poison is used in an amount of 1–10 wt %, preferably 3–6 wt %, of part by weight of hydrazone derivative (I).

The adsorbent to be used in the present invention may be any as long as it adsorbs the reduction catalyst used. Examples thereof include active charcoal, silica gel, alumina gel and the like, with preference given to active charcoal.

The adsorbent is used in an amount of 1–10 wt %, preferably 3–6 wt %, of part by weight of hydrazone derivative (I).

The catalytic poison and/or an adsorbent may be added to a reaction mixture, which is after reaction and before removal of catalyst, or which is after removal of catalyst, with preference given to that after removal of catalyst. After addition of the catalytic poison and/or the adsorbent to the reaction mixture or filtrate, the mixture is thoroughly mixed to deactivate the catalyst. Then any number of the catalyst, catalytic poison and adsorbent contained in the reaction mixture is filtered off and the filtrate is purified to give a highly pure hydrazide derivative (II). The temperature of the catalyst deactivation step is 10–60° C., preferably 20–40° C., and the time necessary for the deactivation is 10 min–60 min.

The hydrazine derivative (II) obtained as above can be purified by a conventional method such as recrystallization, column chromatography and the like. In view of the economic aspect, purification by recrystallization is preferable.

The recrystallization solvent to be used in the present invention is exemplified by saturated hydrocarbon solvent, alcohol solvent, aromatic hydrocarbon solvent, ether solvent and ester solvent As a recrystallization solvent, one or more members of the same group of solvents may be used, or different groups of solvents may be used in combination.

The recrystallization solvent in the present invention is preferably a solvent containing a saturated hydrocarbon solvent. The amount of the saturated hydrocarbon solvent contained in the recrystallization solvent varies depending on the kind of saturated hydrocarbon solvent contained in the recrystallization solvent and the kind of other solvent(s) in the recrystallization solvent. For example, a solvent containing heptane as a saturated hydrocarbon solvent and isopropyl alcohol as a solvent other than the saturated hydrocarbon solvent is a mixed solvent containing 5–20 parts by weight of isopropyl alcohol per 100 parts by weight of heptane.

As the saturated hydrocarbon solvent, for example, pentane, hexane, heptane and the like can be used of these, heptane is preferable because it can be handled easily at a relatively lower vapor pressure. One or more of these saturated hydrocarbon solvents can be used as a recrystallization solvent.

As the alcohol solvent, for example, methanol, ethanol, isopropyl alcohol, butanol, tert-butyl alcohol and the like can be used. One or more of these alcohol solvents can be used as a recrystallization solvent.

As the aromatic hydrocarbon solvent, for example, toluene, benzene and the like can be used. One or more of these aromatic hydrocarbon solvents can be used as a recrystallization solvent.

As the ether solvent, for example, tetrahydrofuran, diethyl ether, 1,2-dimethoxyethane and the like can be used. One or ore of these ether solvents can be used as a recrystallization solvent As the ester solvent for example, ethyl acetate, methyl acetate, butyl acetate and the like can be used. One or more of these ester solvents can be used as a recrystallization solvent.

A recrystallization solvent is used in an amount of 1–10 parts by weight, preferably 2–5 parts by weight, per part by weight of hydrazine derivative (II).

The starting compound, hydrazone derivative (I), is a known compound, and can be obtained by, for example, the reaction of a hydrazine compound (—HN—NH$_2$) and an aldehyde compound (—CHO). To be specific, 4-(pyridin-2-yl)benzaldehyde (III) and tert-butyl carbazate (IV) are reacted to give hydrazone derivative (Ib) (WO97/40029) of the formula

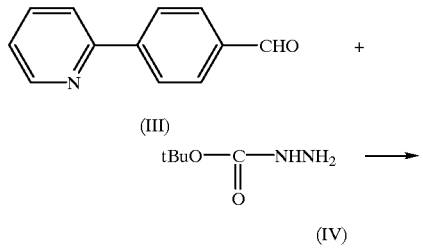

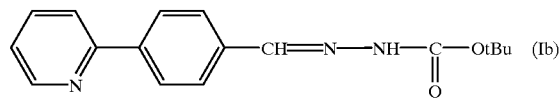

wherein tBu is tert-butyl.

The present invention is explained in detail by referring to illustrative examples. Needless to say, the present invention is not limited to these examples.

REFERENCE EXAMPLE 1

N-(tert-Butoxycarbonyl)-N'-[4-(pyridin-2-yl) phenylmethylidene]hydrazine (20 g, 67.3 mmol), isopropyl alcohol (80 ml) and palladium-carbon (1 g) were charged in a 300 ml four-necked flask and hydrogen was added at 50° C. under atmospheric pressure. Hydrogen was continuously added for 8 hr under the same conditions. The reaction mixture was filtered to remove the catalyst. After 90% of isopropyl alcohol in the obtained filtrate was evaporated by concentration, the same volume of heptane was added. The mixture was cooled with stirring and crystals were precipitated at around 40° C. The mixture was further cooled to 5° C. with stirring and the precipitated crystals were collected by filtration and dried to give 16.91 g of tert-butyl3-[4-(pyridin-2-yl)benzyl]carbazate as white crystals. The yield was 84.0% of N-(tert-butoxycarbonyl)-N'-[4-5 (pyridin-2-yl )phenylmethylidene]hydrazine Then, the obtained tert-butyl3-[4-(pyridin-2-yl)benzyl] carbazate (20 mg) was dissolved in isopropyl alcohol to the total amount of 20 ml and subjected to IPLC. As a result, the area percentage was 99.56% and the peak of N-(tert-butoxycarbonyl)-N'-10 [4-(pyridin-2-yl) phenylmethylidene]hydrazine was not detected. This solution was left standing at room temperature for 22 hr and again subjected to HPLC. As a result, the area percentage was 99.49% and N-(tert-butoxycarbonyl)-N'-[4-(pyridin-2-yl) phenylmethylidene]-hydrazine was found to have been generated by 0.06%.

REFERENCE EXAMPLE 2

To tert-butyl3-[4- (pyridin-2-yl ) benzyl carbazate (20 mg) obtained in Reference Example 1 was added isopropyl alcohol to the total amount of 20 ml, to which palladium-carbon (2 mg) was added. This solution was left standing at room temperature for 22 hr and subjected to EPLC. As a result, N-(tert-butoxycarbonyl)-N'-[4-(pyridin-2-yl) phenylmethylidenelhydrazine was found to have been generated by 1.2%.

EXAMPLE 1

N-(tert-Butoxycarbonyl-N'-4- (pyridin-2yl) phenylmzethylidene]hydrazine (26 g, 67.3 mmol)) isopropyl alcohol (80 ml) and palladium-carbon (1 g) were charged in a 300 ml four-necked flask, and hydrogen was added at 50° C. under atmospheric pressure. Hydrogen was continuously added for 8 hr under the same conditions. The reaction mixture was filtered to remove the catalyst. Sodium hydrosulfite (1 g) and active charcoal (1 g) were added to the filtrate and the mixture was stirred at 20–30° C. for 30 min. The reaction mixture was filtered to reeve sodium hydrosulfite and active charcoal. After 90% of isopropyl alcohol in the obtained filtrate was evaporated by concentration, the same volume of heptane was added. The mixture was cooled with stirring and crystals were precipitated at around 40° C.

The mixture was further cooled to 5° C. with stirring and the precipitated crystals were collected by filtration and dried to give 16.84 g of tert-butyl3-(4-(pyridin-2-yl)benzyl]carbazate as white crystals. The yield was 83.6% of N-(tert-butoxycarbonyl)-N'-[4-(pyridin-2-yl)phenylmethylidene]hydrazine.

Then,the obtained tert-butyl3-[4-(pyridin-2-yl)benzyl]carbazate (20 mg) was dissolved in isópropyl alcohol to the total amount of 20 ml and subjected to HPLC. As a result, the area percentage was 99.64% and the peak of N-(tert-butoxycarbonyl)-N'-[4-(pyridin-2-yl)phenylmethylidene]hydrazine was not detected. This solution was left standing at room temperature for 26 hr and again subjected to EPLC. As a result, the area percentage was 99.65% and the peak of N-(tert-butoxycarbonyl)-N'-[4-(pyridin-2-yl)phenylmethylidene]hydrazine was not detected.

When hydrazine derivative (IIb) obtained by a known method was dissolved in isopropyl alcohol and the resulting solution was left standing at room temperature for 22 hr, the original hydrazone derivative (Ib) was found present. In contrast, when the hydrazine derivative (IIb) obtained by the production method of the present invention was left standing for 4 more hours under the same conditions, it did not return to the original hydrazone derivative (Ib) but showed a high purity of hydrazine derivative (IIb).

According to the production method of the present invention, hydrazine derivative (II) stable even in a solution state can be produced in addition, the production method of the present invention is industrially superior.

What is claimed is:

1. A method of producing a hydrazine derivative of the formula (IIa)

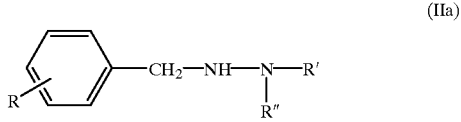

(IIa)

wherein R is hydrogen atom, halogen atom, alkyl having 1 to 4 carbon atoms, alkoxy having 1 to 4 carbon atoms, optionally substituted aryl or optionally substituted aromatic heterocyclic group, R' is hydrogen atom, acyl, alkoxycarbonyl, alkyl or optionally substituted phenyl and R" is acyl, alkoxycarbonyl, alkyl or optionally substituted phenyl, which comprises subjecting a hydrazone derivative of the formula (Ia)

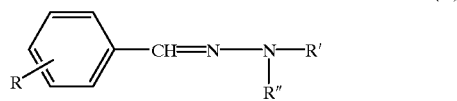

(Ia)

wherein R, R' and R" are as defined above, to catalytic reduction and deactivating the reduction catalyst contained in the reaction mixture thereof, so as to produce a hydrazine derivative.

2. The production method of claim 1, wherein R is hydrogen atom, fluorine, bromine, chlorine, t-butyl, methoxy, ethoxy, phenyl, naphthyl, furyl, oxazolyl, imidazolyl, pyridyl, or pyrimidyl, R' is hydrogen atom, acetyl, benzoyl, t-butoxycarbonyl, methyl, ethyl, propyl, or optionally substituted phenyl, and R" is acetyl, benzoyl, t-butoxycarbonyl, methyl, ethyl, propyl, or optionally substituted phenyl.

3. The production method of claim 1, wherein the step for deactivating the reduction catalyst comprises the use of a catalytic poison comprising an element from Group Va or VIa or an adsorbent or catalytic poison comprising an element from Group Va or VIa and an adsorbent.

4. The production method of claim 3, wherein the catalytic poison is a sulfur compound.

5. The production method of claim 4, wherein the sulfur compound a sodium hydrosulfite.

6. The production method of claim 3, wherein the adsorbent is an active charcoal.

7. The production method of claim 1, which further comprise, after deactivation of the reduction catalyst, recrystallizing in a solvent containing a saturated hydrocarbon solvent.

8. The production method of claim 1, wherein the hydrazine derivative (II) is tert-butyl3-[4-(pyridin-2-yl)benzyl]carbazate.

9. The production method of claim 2, wherein the hydrazine derivative (II) is tert-butyl3-[4-(pyridin-2-yl)benzyl]carbazate.

10. The production method of claim 3, wherein the hydrazine derivative (II) is tert-butyl3-[4-(pyridin-2-yl)benzyl]carbazate.

11. The production method of claim 4, wherein the hydrazine derivative (II) is tert-butyl3-[4-(pyridin-2-yl)benzyl]carbazate.

12. The production method of claim 5, wherein the hydrazine derivative (II) is tert-butyl3-[4-(pyridin-2-yl)benzyl]carbazate.

13. The production method of claim 6, wherein the hydrazine derivative (II) is tert-butyl3-[4-(pyridin-2-yl)benzyl]carbazate.

14. The production method of claim 7, wherein the hydrazine derivative (II) is tert-butyl3-[4-(pyridin-2-yl)benzyl]carbazate.

15. The production method of claim 1, wherein the hydrazine derivative is stable in solution.

* * * * *

UNITED STATES PATENT AND TRADEMARK OFFICE
CERTIFICATE OF CORRECTION

PATENT NO.    : 6,376,678 B1
DATED         : April 23, 2002
INVENTOR(S)   : Sugi et al.

It is certified that error appears in the above-identified patent and that said Letters Patent is hereby corrected as shown below:

Column 1,
Line 47, "hydrazone -drivative" should read -- hydrazone derivative --.
Line 52, "tert-butyl3-[4-(pyridin-2-yl)benzyllcarbazate" should read
-- tert-butyl 3-[4-(pyridin-2-yl)benzyl]carbazate --.

Column 2,
Lines 47-48, "solvents Accordingly" should read -- solvents. Accordingly --.

Column 3,
Line 12, "alkyl -or" should read -- alkyl or --.
Lines 36-37, "tert-butyl3-[4-(pyridin-2-yl)benzyl]carbazate" should read
-- tert-butyl 3-[4-(pyridin-2-yl)benzyl]carbazate --.
Line 51, "alkoxy" should read -- alkyl --.
Line 55, "alkyl" should read -- alkoxy --.

Column 4,
Line 14, "inventions." should read -- invention. --.
Line 20, "phenyl The" should read -- phenyl. The --.
Line 65, "as" should read -- is --.

Column 5,
Line 3, "State." should read -- state. --.
Lines 33-34, "tert-butyl3-f4-(pyridin-2-yl)benzyl]carbazate" should read
-- tert-butyl 3-[4-(pyridin-2-yl)benzyl]carbazate. --

Column 6,
Line 8, "(S, se, Te)" should read -- (S, Se, Te) --.
Line 26, "—SHf" should read -- —SH --.
Line 59, "Then any" should read -- Then, any --.
Line 62, "hydrazide" should read -- hydrazine --.

Column 7,
Line 6, "solvent As" should read -- solvent. As --.
Line 40, "ore" should read -- more --.

UNITED STATES PATENT AND TRADEMARK OFFICE
CERTIFICATE OF CORRECTION

PATENT NO. : 6,376,678 B1
DATED : April 23, 2002
INVENTOR(S) : Sugi et al.

It is certified that error appears in the above-identified patent and that said Letters Patent is hereby corrected as shown below:

<u>Column 8,</u>
Lines 26-27, "tert-butyl3-[4-(pyridin-2-yl)benzyl]carbazate" should read
-- tert-butyl 3-[4-(pyridin-2-yl)benzyl]carbazate --.
Lines 30-31, "tert-butyl3-[4-(pyridin-2-yl)benzyl]carbazate" should read
-- tert-butyl 3-[4-(pyridin-2-yl)benzyl]carbazate --.
Line 32, "IPLC." should read -- HPLC. --.
Line 44, "tert-butyl3-[4- (pyridin-2-yl) benzyl carbazate" should read
-- tert-butyl 3-[4-(pyridin-2-yl)benzyl]carbazate --.
Line 48, "EPLC." should read -- HPLC. --.
Lines 49-50, "N-(tert-butoxycarbonyl)-N'-[4-(pyridin-2-yl)
phenylmethylidenelhydrazine" should read -- N-(tert-butoxycarbonyl)-N'-[4-(pyridin-2-yl)phenylmethylidene]hydrazine --.
Lines 54-55, "N-(tert-Butoxycarbonyl)-N'-[4- (pyridin-2-yl)phenylmzethylidene]
hydrazine" should read -- N-(tert-butoxycarbonyl)-N'-[4-(pyridin-2-yl)
phenylmethylidene]hydrazine --.
Line 63, "reeve" should read -- remove --.

<u>Column 9,</u>
Lines 3-4, "tert-butyl3-(4-(pyridin-2-yl)benzyl]carbazate" should read
-- tert-butyl 3-[4-(pyridin-2-yl)benzyl]carbazate --.
Lines 7-8, "tert-butyl3-[4-(pyridin-2-yl)benzyl]carbazate" should read
-- tert-butyl 3-[4-(pyridin-2-yl)benzyl]carbazate --.
Line 8, "is6propyl" should read -- isopropyl --.
Line 12, "EPLC." should read -- HPLC. --.

UNITED STATES PATENT AND TRADEMARK OFFICE
CERTIFICATE OF CORRECTION

PATENT NO.    : 6,376,678 B1
DATED         : April 23, 2002
INVENTOR(S)   : Sugi et al.

It is certified that error appears in the above-identified patent and that said Letters Patent is hereby corrected as shown below:

<u>Column 10,</u>
Line 19, "a" should read -- is --.
Lines 29-30, "tert-butyl3-[4-(pyridin-2-yl)benzyl]carbazate" should read
-- tert-butyl 3-[4-(pyridin-2-yl)benzyl]carbazate --.
Lines 33-34, "tert-butyl3-[4-(pyridin-2-yl)benzyl]carbazate" should read
-- tert-butyl 3-[4-(pyridin-2-yl)benzyl]carbazate --.
Lines 36-37, "tert-butyl3-[4-(pyridin-2-yl)benzyl]carbazate" should read
-- tert-butyl 3-[4-(pyridin-2-yl)benzyl]carbazate --.
Lines 39-40, "tert-butyl3-[4-(pyridin-2-yl)benzyl]carbazate" should read
-- tert-butyl 3-[4-(pyridin-2-yl)benzyl]carbazate --.
Lines 43-44, "tert-butyl3-[4-(pyridin-2-yl)benzyl]carbazate" should read
-- tert-butyl 3-[4-(pyridin-2-yl)benzyl]carbazate --.
Lines 46-47, "tert-butyl3-[4-(pyridin-2-yl)benzyl]carbazate" should read
-- tert-butyl 3-[4-(pyridin-2-yl)benzyl]carbazate --.
Lines 50-51, "tert-butyl3-[4-(pyridin-2-yl)benzyl]carbazate" should read
-- tert-butyl 3-[4-(pyridin-2-yl)benzyl]carbazate --.

Signed and Sealed this

Twenty-fifth Day of February, 2003

JAMES E. ROGAN
*Director of the United States Patent and Trademark Office*